(12) United States Patent
Seethala et al.

(10) Patent No.: US 7,384,757 B2
(45) Date of Patent: Jun. 10, 2008

(54) SCINTILLATION PROXIMITY ASSAY METHOD OF MEASURING ACETYL COA CARBOXYLASE ENZYME ACTIVITY

(75) Inventors: Ramakrishna Seethala, West Windsor, NJ (US); Dong Cheng, Furlong, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/093,428

(22) Filed: Mar. 30, 2005

(65) Prior Publication Data
US 2005/0221410 A1    Oct. 6, 2005

Related U.S. Application Data

(60) Provisional application No. 60/558,015, filed on Mar. 31, 2004.

(51) Int. Cl.
G01N 33/53 (2006.01)
C12Q 1/48 (2006.01)
C12N 9/00 (2006.01)

(52) U.S. Cl. .................... 435/7.6; 435/15; 435/183
(58) Field of Classification Search ............... None
See application file for complete search history.

(56) References Cited

U.S. PATENT DOCUMENTS 6,994,956 B2 *    2/2006   Landro et al. ............... 435/4

OTHER PUBLICATIONS

Weiss et al. Characterization of Fatty Acid Synthase Activity Using Scintillation Proximity; Assay and Drug Development Technologies, vol. 1, No. 1-2 (2003) pp. 161-166.*
Beaty et al. Kinetics of Activation of Acetyl-CoA Crboxylase by Citrate; The Journal of Biological Chemistry, vol. 258, No. 21 (1983) pp. 13043-13050.*
Abu-Elheiga, et al., "Acetyl-CoA carboxylase 2 mutant mice are protected against obesity and diabetes induced by high-fat/high-carbohydrate diets", PNAS, vol. 100 (18), pp. 10207-10212 (2003).
Abu-Elheiga, et al., "Continuous Fatty Acid Oxidation and Reduced Fat Storage in Mice Lacking Acetyl-CoA Carboxylase 2", Science, vol. 291, pp. 2613-2616 (2001).
Beaty, et al., "Acetyl Coenzyme A Carboxylase", JBC, vol. 257 (2), pp. 924-929 (1982).
Harwood, et al., "Isozyme-nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals", JBC, vol. 278 (39), pp. 37099-37111 (2003).
Jamil, et al., "Phosphorylation State of Acetyl-coenzyme A Carboxylase", JBC, vol. 262 (2), pp. 630-637 (1987).
Ramakrishna, et al., "Rapid Purification of Enzymes of Fatty Acid Biosynthesis From Rat Adipose Tissue", Preparative Biochemistry, vol. 13 (5), pp. 475-488 (1983).
Tanabe, et al., "Acetyl-CoA Carboxylase from Rat Liver", Methods Enzymol., vol. 71 (Pt C), pp. 5-16 (1981).
Waite, et al., "Studies on the Mechanism of Fatty Acid Synthesis", JBC, vol. 237 (9), pp. 2750-2757 (1962).
Wakil, et al., "Studies on the Mechanism of Fatty Acid Synthesis", Biochim. Biophys. Acta, vol. 34, pp. 227-233 (1959).
NCBI Entrez Accession No. J04485 (gi:460908), Huang, et al., Mar. 13, 1995.
NCBI Entrez Accession No. NM_017332 (gi:8394157), Rumberger, et. al., Apr. 15, 2005.
NCBI Entrez Accession No. NM_007988 (gi:30911098), Schmid, et al., Apr. 15, 2005.
NCBI Entrez Accession No. U26644 (gi:1049052), Jayakumar, et al., Nov. 8, 1995.

* cited by examiner

*Primary Examiner*—Jon Weber
*Assistant Examiner*—Paul C. Martin
(74) *Attorney, Agent, or Firm*—Brian C. Carey

(57) ABSTRACT

The present invention relates generally to enzyme assays and more particularly to a rapid, sensitive, reliable and robust homogeneous assay for acetyl CoA carboxylase activity comprising a coupled enzyme assay in a scintillation proximity format suitable for high-throughput screening. In one aspect, the assay couples ACC and FAS and the product, palmitic acid is then detected by scintillation counting. The invention also relates to the identification of modulators of ACC activity.

10 Claims, 12 Drawing Sheets

FIG. 1

ACC-biotin + $Mg^{2+}$-ATP + $HCO_3$ ⟶ ACC-biotin-$CO_2$ + $Mg^{2+}$-ADP + Pi

ACC-biotin-$CO_2$ + Acetyl CoA ⟶ Malonyl CoA + ACC-biotin

---

$HCO_3^-$ + $Mg^{2+}$-ATP + + Acetyl CoA $\xrightarrow{\text{ACC-biotin}}$ Malonyl CoA + $Mg^{2+}$-ADP + Pi

FIG. 2

Scheme 1
$^{14}CO_2$ Fixation Assay

Acetyl CoA + [$^{14}$C]HCO$_3^-$ + ATP $\xrightarrow{ACC}$ [$^{14}$C]Malonyl CoA + ADP + Pi

Scheme 2
Measuring ADP in a Coupled Enzyme Assay

Acetyl CoA + HCO$_3^-$ + ATP $\xrightarrow{ACC}$ Malonyl CoA + ADP + Pi

PEP + ADP $\xrightarrow{PK}$ Pyruvate + ATP

Pyruvate + NADH $\xrightarrow{PDH}$ Lactate + NAD$^+$ + H$^+$

Scheme 3
ACC/FAS Coupled Enzyme Assay

Acetyl CoA + HCO$_3^-$ + Mg$^{2+}$·ATP $\xrightarrow{ACC}$ Malonyl CoA + Mg$^{2+}$·ADP + Pi Acetyl CoA + 7 Malonyl CoA + 14 NADPH + 14 H$^+$ $\xrightarrow{FAS}$
Palmitate + 14 NADP + 8CoA + 7CO$_2$ + 6H$_2$O Overall Reaction:

8Acetyl CoA + 7HCO$_3$ + 7ATP + 14 NADPH + 14H$^+$ $\xrightarrow{ACC, FAS}$
Palmitate + 7ADP + 7Pi + 14 NADP + 8 CoA + 7 CO$_2$ + 6 H$_2$O ACC/FAS coupled SPA assay HCO$_3^-$ + [$^3$H]Acetyl CoA $\Big\downarrow$ *ACC + FAS*
*Mg-ATP + Citrate + NADPH*

[$^3$H] Palmitic acid

FIG. 4

Frozen Liver /thaw in buffer @ RT

Homogenization(Polytron 4x1min)

Centrifugation @ 25000 x g/30min
and @ 100,000 x g/1h

AS fractionation 0-45%

Affinity purified
(3rd day morning)

Affinity Chromatography on Avidin-Sep
Mix with monomeric avidin-Sep O/N @ 5°C
Wash avidin gel on a funnel, load in a column
and elute with biotin. Pool active fractions.
Concentrate by AS pptn, dialyze and store at -80°C Partially purified FAS (end of 2nd day)

Avidin-Sep FT pptd with 10-15% PEG
Batch loaded on DEAE Sephacel
Washed on a funnel
FAS eluted with 250 mM PO$_4$

US 7,384,757 B2

SCINTILLATION PROXIMITY ASSAY METHOD OF MEASURING ACETYL COA CARBOXYLASE ENZYME ACTIVITY

This application claims priority under 35 U.S.C. §119(e) to U.S. Provisional application Ser. No. 60/558,015, filed on Mar. 31, 2004, the contents of which are hereby incorporated by reference in their entirety.

FIELD OF THE INVENTION

The present invention relates generally to assays of ACC activity and more particularly to a rapid, sensitive, reliable and robust assay for acetyl CoA carboxylase activity comprising a coupled assay suitable for high-throughput screening. The invention also relates to methods of identifying modulators of ACC activity.

BACKGROUND OF THE INVENTION

Acetyl CoA carboxylase (ACC) is the rate-determining enzyme of fatty acid biosynthesis in plants and animals. ACC is a biotin containing enzyme which catalyzes the carboxylation of acetyl CoA to form malonyl CoA in a two-step reaction (Beaty & Lane, (1982). *J. Biol. Chem.* 257:924-929). The first step is the ATP-dependent carboxylation of biotin covalently linked to the enzyme. In the second step, a carboxyltransferase step, the carboxyl group is transferred to the substrate, acetyl CoA, to form malonyl CoA (FIG. 1). Citrate is a potent allosteric activator of ACC. Malonyl CoA is the C2 donor for de novo synthesis of long chain fatty acids.

In mammals, there are two subtypes of ACC, ACC1 and ACC2. ACC1 is mainly localized in lipogenic tissues such as adipose tissue and liver, where fatty acids are synthesized. ACC2 is found primarily in non-lipogenic tissues such as skeletal muscle and heart muscle, although some is also found in liver. Malonyl CoA allosterically inhibits carnitine palmitoyl transferase 1 (CPT1), which is a critical enzyme to transfer the long chain fatty acid into the mitochondria for β-oxidation. Because ACC2 is co-localized with CPT-1, the primary role of malonyl CoA that is synthesized by ACC2 has been suggested to regulate the rate of β-oxidation.

ACC is a potential target in metabolic diseases for the treatment of metabolic syndrome including obesity, insulin resistance and dyslipidemia. Increased rates of muscle fatty acid oxidation, a reduced fat content and a reduction in total body fat were observed in ACC-2 knock-out mice (Abu-Elheiga et al., (2001) *Science* 291:2613-2616; Abu-Elheiga et al., (2003) *Proc. Natl. Acad. Sci. USA*. 100:10207-10212). Harwood et al. reported that ACC inhibitors caused reduction in fatty acid synthesis, increase in fatty acid oxidation, and reduction of respiratory quotient in rats (Harwood et al., (2003) *J. Biol. Chem.* 278:37099-37111). Chronic dosing of these compounds resulted in the reduction of whole body fat mass and improvement of insulin sensitivity (Harwood et al., (2003) *J. Biol. Chem.* 278:37099-37111). These observations further validated the enzyme as a drug target.

Despite the importance of ACC in the discovery and development of ACC inhibitors as drugs for the treatment of metabolic diseases, technical difficulties associated with ACC have greatly hindered progress in this area. One of the technical challenges has been the lack of a convenient, robust, economical enzyme assay that would allow high-throughput screening (HTS) for ACC inhibitors in an efficient manner. A $CO_2$-fixation assay is the most commonly used ACC assay (FIG. 2, scheme 1). In this assay, $[^{14}C]$— $NaHCO_3$, acetyl CoA, Mg-ATP, citrate and ACC are incubated at 37° C.; the reaction mixture is quenched with acid at the end of the reaction, followed by heating to remove bicarbonate as $^{14}CO_2$. Scintillant is then added and the acid-stable malonyl CoA remaining in the vial is counted in a scintillation counter (Waite, M., and Wakil, S. J. (1962) *J. Biol. Chem.* 237:2750-2757, Tanabe et al., (1981) *Methods Enzymol.* 71 Pt C, 5-16). This is a multi-step radioactive assay, which is time consuming and labor-intensive. Further, this assay requires large amounts of radioactivity, and special laboratory design to trap $^{14}CO_2$ liberated in the assay. Although the assay can be run using a 96-well microtiter plate format, at best it is a low-throughput assay format and not suitable for HTS.

The continuous ATP regeneration-coupled spectrophotometric assay is another assay format. In this type of assay, the ADP generated in the ACC enzyme reaction is converted to ATP by a pyruvate kinase/lactate dehydrogenase coupled enzyme system, and NADH disappearance is followed at 340 nm spectrophotometrically or fluorometrically (Tanabe et al., (1981) *Methods Enzymol.* 71 Pt C, 5-16; FIG. 2, scheme 2). The ATP-regeneration system is very sensitive to the presence of ATPases. Since ATPase is highly abundant in tissue or cell culture extract, a disadvantage of this assay is that it demands highly pure ACC protein (about 5 μg/assay) and is less sensitive. Additionally, colored compounds that have absorption at 340 nm wave length may give false negatives in the screening.

Yet another form of ACC assay is an ACC/FAS coupled assay (FIG. 2, scheme 3). In the ACC reaction, malonyl CoA is formed from acetyl CoA. Malonyl CoA can then be used as a substrate for FAS with NADPH as the cofactor. The reaction can be monitored by the rate of utilization of NADPH spectrophotometrically (Wakil et al., (1959) *Biochim. Biophys. Acta* 34:227-233). However, this ACC/FAS spectrophotometric coupled assay requires large amounts of pure ACC and FAS enzymes, making this assay potentially expensive, and very time and resource intensive. Further, the rate of NADPH utilization has to be measured kinetically making the assay less amenable for HTS.

The assays discussed above are not practical for HTS, which requires a robust, reliable homogeneous assay that requires only small amounts of the enzymes. To fill this long-felt need, the inventors developed a homogenous ACC assay in which ACC is coupled to FAS and the product, palmitic acid, is detected by scintillation proximity. This assay can be particularly powerful for HTS of potential ACC modulators. The present assay can be used routinely for compound evaluation and can be employed to establish structure activity relationships.

SUMMARY OF THE INVENTION

The present invention relates generally to scintillation proximity assays and more particularly to a rapid, sensitive, reliable and robust homogeneous assay for acetyl CoA carboxylase comprising a coupled assay in a scintillation proximity format suitable for high-throughput screening.

In one aspect of the present invention a method of assaying ACC catalytic activity is provided. In one embodiment, the method comprises: (a) contacting an enzyme mix comprising ACC and FAS, optionally comprising one or more of bicarbonate, Mg, ATP, NADPH and an ACC effector, with a solid support comprising a scintillant and a linking moiety; (b) incubating the enzyme mix with an acetyl CoA mix comprising radiolabeled acetyl CoA, optionally comprising one or more of bicarbonate, Mg, ATP, NADPH and an ACC effector, under suitable reaction conditions, for a desired incubation time; and (c) detecting scintillation signal, wherein scintillation signal is indicative of ACC catalytic activity.

In the method, the ACC can be mammalian ACC1, ACC2, animal ACC or plant ACC. When the ACC is ACC2, the ACC2 can comprise the amino acid sequence of human ACC2, or an ortholog, such as rat ACC2 (GENBANK® ID No. NP_446374). When the ACC is ACC1, the ACC1 can comprise rat ACC1, and can comprise the amino acid sequence of GENBANK® ID No. P11497, for example, or human ACC1 (GENBANK® ID No. AAP94122). Any solid support can be employed in the method, including a welled plate, such as a 96- or 384-welled plate. In another example, a SPA bead comprising a hydrophobic moiety or group may be used as a solid support and can facilitate the association of the product of the ACC/FAS coupled enzyme reaction that gives scintillant signal. The scintillant can comprise any material that is adapted to emit energy under a particular set of conditions. The linking moiety can be any entity that is adapted to associate the product of the ACC/FAS coupled enzyme reaction with the solid support, for example a phospholipid, which can associate the reaction product with the solid support via a hydrophobic interaction. A radiolabel can be any label that is adapted to precipitate energy emission from the solid support; preferably a weak beta emitter is employed. An example of a suitable radiolabel, is tritium. The ACC effector can be any effector, although citrate is preferred.

In another aspect of the present invention, a method of identifying a modulator of ACC catalytic activity is provided. In one embodiment, the method comprises: (a) measuring ACC catalytic activity in the absence of a test compound; (b) contacting an enzyme mix comprising ACC, FAS, and a test compound, optionally comprising one or more of bicarbonate, Mg, ATP, NADPH and an ACC effector, with a solid support comprising a scintillant and a linking moiety; (c) incubating the enzyme mix and the test compound with acetyl CoA mix comprising labeled acetyl CoA, optionally comprising one or more of bicarbonate, Mg, ATP, NADPH and an ACC effector, under suitable reaction conditions, for a desired incubation time; and (d) detecting scintillation signal in the presence of the test compound; wherein a difference between ACC catalytic activity detected in the presence of the test compound compared to ACC catalytic activity detected in the absence of the test compound indicates the test compound is a modulator of ACC catalytic activity. The method can further comprise the optional step of correlating scintillation signal in the presence of the test compound with ACC catalytic activity, In the method, the ACC can be mammalian ACC1, ACC2, animal ACC or plant ACC. When the ACC is ACC2, the ACC2 can comprise the amino acid sequence of human ACC2, or an ortholog, such as rat ACC2 (GENBANK® ID No. NP_446374). When the ACC is ACC1, the ACC1 can comprise rat ACC1, and can comprise the amino acid sequence of GENBANK® ID No. P11497, for example, or human ACC1 (GENBANK® ID No. AAP94122). Any solid support can be employed in the method, including a welled plate, such as a 96- or 384-welled plate. In another example, a SPA bead comprising a hydrophobic moiety or group may be used as a solid support and can facilitate the association of the product of the ACC/FAS coupled enzyme reaction that gives scintillant signal. The linking moiety can be any entity that is adapted to associate the product of the ACC/FAS coupled enzyme reaction with the solid support, for example a phospholipid, which can associate the reaction product with the solid support via a hydrophobic interaction. Additionally, a radiolabel can be any label that is adapted to precipitate energy emission from the solid support; preferably a weak beta emitter is employed. An example of a suitable radiolabel, is tritium. The ACC effector can be any effector, although citrate is preferred.

In a further aspect of the present invention a kit is provided for assaying ACC catalytic activity. In one embodiment the kit comprises: (a) a container containing an enzyme mix comprising FAS, and optionally containing one or more of bicarbonate, Mg, ATP, NADPH and an ACC effector; (b) a container containing an acetyl CoA mix comprising radiolabeled acetyl CoA, and optionally comprising one or more of bicarbonate, Mg, ATP, NADPH and an ACC effector; and (c) a solid support comprising a scintillant and a linking moiety.

In the kit, the ACC can be ACC1 or ACC2. When the ACC is ACC1, the ACC1 can comprise rat ACC1. Any solid support can be employed in the kit, including a welled plate, such as a 96- or 384-welled plate. In another example, a SPA bead comprising a hydrophobic moiety or group may be used as a solid support and can facilitate the association of the product of the ACC/FAS coupled enzyme reaction that gives scintillant signal. The scintillant can comprise any material that is adapted to emit energy under a particular set of conditions. The linking moiety can be any entity that is adapted to associate the product of the ACC/FAS coupled enzyme reaction with the solid support, for example a phospholipid, which can associate the reaction product with the solid support via a hydrophobic interaction. Additionally, the radiolabel can be any label that is adapted to precipitate energy emission from the solid support. An example of a suitable radiolabel, is tritium. The ACC effector can be any effector, although citrate is preferred.

Accordingly, it is an object of the present invention to provide a novel method of identifying modulators of ACC activity. This and other objects are achieved in whole or in part by the present invention.

An object of the invention having been stated, other objects will be evident as the description proceeds, when taken in connection with the accompanying Drawings and Examples as described herein below.

BRIEF DESCRIPTION OF THE DRAWINGS

FIG. 1 is a reaction diagram depicting the individual steps of, and overall, ACC reaction.

FIG. 2 depicts several prior art methods of determining ACC activity, (schemes 1-3).

FIG. 4 is a flowchart depicting a method of purifying ACC and FAS enzymes, which can be employed in the assay of the present invention.

DETAILED DESCRIPTION OF THE INVENTION

Figure 3:
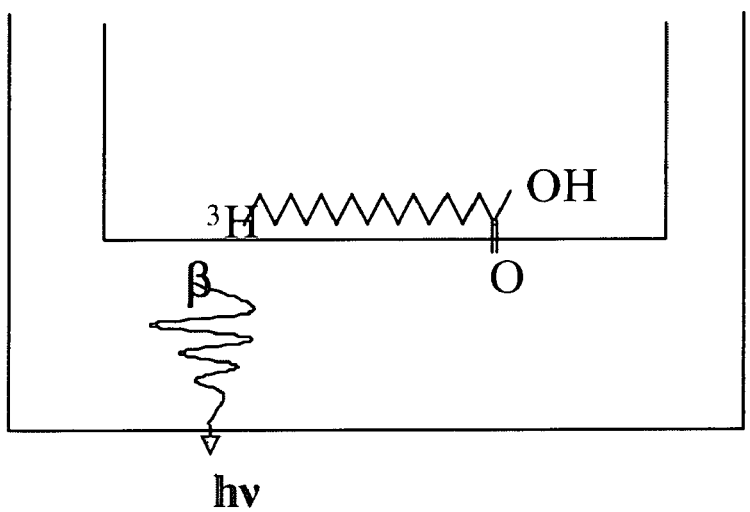
FIG. 3 is diagram graphically depicting an ACC/FAS coupled enzyme assay of the present invention.

The present invention relates to a method of determining ACC activity and is adapted for HTS applications. In one embodiment, the assay comprises incubating [$^3$H]-acetyl CoA, bicarbonate and effectors of ACC with ACC, FAS and NADPH in a phospholipid-coated solid support comprising a trapped scintillant, such as a phospholipid- and scintillant-coated 384-well plate (e.g., a phospholipid-coated FLASH-PLATE™, available from PerkinElmer, Boston, Mass.). Under reaction conditions, [$^3$H]-malonyl CoA is formed from [$^3$H]-acetyl CoA via the ACC reaction. The synthesized malonyl CoA and unreacted [$^3$H]-acetyl CoA then serve as the substrates for the FAS reaction, which produces [$^3$H]-palmitic acid. The [$^3$H]-palmitic acid formed in the ACC/FAS coupled assay then associates with a linking moiety which is itself associated with a solid support comprising a scintillant (e.g., the phospholipid component of a phospholipid-coated solid support) via hydrophobic interactions. The association of the radiolabeled palmitic acid reaction product with the linking moiety brings the palmitic acid into close proximity with the scintillant, which in turn generates scintillation signal which can be read in a scintillation counter, such as a TOPCOUNT™ scintillation counter (PerkinElmer Boston, Mass.). Due in part to the suitability of the assay to a multiwelled plate format, the assay can be employed HTS operations and is a significant advancement over the time and resource intensive ACC activity assays presently being employed by researchers in the field.

I. Definitions

Following long-standing patent law convention, the terms "a" and "an" mean "one or more" when used in this application, including the claims.

As used herein, the term "ACC" means the enzyme Acetyl CoA Carboxylase. The term encompasses all forms of ACC, including mammalian ACC1, ACC2 and plant ACC. Further, the term ACC is not limited to enzyme derived from a particular species; thus, it is intended that all ACC orthologs are encompassed by the term ACC, including human ACC1 and ACC2 enzymes and rat ACC1 and ACC2 enzymes. The term also encompasses fragments of ACC that exhibit catalytic activity, namely the ability to convert acetyl CoA to malonyl CoA. An example of ACC2 is human ACC2. An example of ACC1 is rat ACC1. The term ACC also encompasses ACC sequences comprising one or more mutations in the amino acid sequence. Such mutations can be naturally occurring or can be engineered using standard mutatgenesis techniques known in the art.

As used herein, the term "FAS" means the enzyme Fatty Acid Synthase. The term encompasses all forms of FAS. Further, the term FAS is not limited to enzyme derived from a particular species; thus, it is intended that all FAS orthologs are encompassed by the term FAS, including human and rat FAS and FAS. The term also encompasses fragments of FAS that exhibit catalytic activity, namely the ability to convert malonyl CoA and acetyl CoA to palmitic acid. Thus the term includes segments of FAS that are shorter than full-length FAS, but which still retain catalytic activity. An example of an FAS is rat FAS (GENBANK® ID No. NM_017332); other examples include human, mouse and chicken FAS (GENBANK® ID Nos. U26644, NM_007988, and J04485, respectively). The term FAS also encompasses FAS sequences comprising one or more mutations in the amino acid sequence. Such mutations can be naturally occurring or can be engineered using standard mutagenesis techniques known in the art.

As used herein, the term "high-throughput screening" means any method or operation by which a plurality of test samples are analyzed for one or more properties, such as ACC modulation. A high-throughput operation is preferably automated.

As used herein, the term "linking moiety" means any chemical compound adapted to associate with the palmitic acid product of the ACC/FAS coupled enzyme reaction. A linking moiety must also be adapted to associate with the solid support that is selected. A function of a linking moiety is to bring the ACC/FAS reaction product palmitic acid into proximity with the scintillant, which is associated with the solid support. Consequently, any entity capable of fulfilling this role can be employed as a linking moiety. The use of a phospholipid as a linking moiety is described herein and is preferred.

As used herein the term "solid support" means any vessel in which the coupled enzyme reaction can be carried out. A non-limiting example of a "solid support" is a welled plate, such as a 384 welled plate. Another example is a bead, such as a commercially available SPA bead.

As used herein, the term "test compound" means a substance known or suspected to interact with a complete ACC polypeptide or a fragment thereof. Representative test compounds include "xenobiotics", such as drugs and other therapeutic agents, carcinogens and environmental pollutants, natural products and extracts, as well as "endobiotics", such as steroids, fatty acids and prostaglandins. Other examples of test compounds that can be investigated using the methods of the present invention include, but are not restricted to, activators and inhibitors of ACC, hormones (e.g., opioid peptides, steroids, etc.), peptides, enzyme substrates, co-factors, lectins, sugars, oligonucleotides, proteins, small molecules and monoclonal antibodies.

II. Preparation of ACC and FAS Enzymes

ACC and/or FAS, can be isolated from any suitable animal source, for example from mammalian (e.g., rat) or chicken livers, mammalian or chicken adipose tissue, mammalian or chicken skeletal muscle and/or mammalian or chicken heart muscle. ACC and/or FAS can be isolated from a biological sample using standard protein purification methodology known to those of the art (see, e.g., Janson, *Protein Purification: Principles, High Resolution Methods, and Applications*, (2$^{nd}$ ed.) Wiley, New York, (1997); Rosenberg, *Protein Analysis and Purification: Benchtop Techniques*, Birkhauser, Boston, (1996); Walker, *The Protein Protocols Handbook*, Humana Press, Totowa, N.J., (1996); Doonan, *Protein Purification Protocols*, Humana Press, Totowa, N.J., (1996); Scopes, *Protein Purification: Principles and Practice*, Springer-Verlag, New York, (1994); Harris, *Protein Purification Methods: A Practical Approach*, IRL Press, New York, (1989), all of which are incorporated in their entireties herein by reference). Guidance in the isolation of an ACC and/or FAS is provided herein, for example in the Examples (see Example 1) and in the Drawings (see FIG. 4). Other methods of purifying active ACC and FAS may be known to those of skill in the art and any such methods can be employed in the present invention.

In some situations, it may be desirable to recombinantly express the enzymes of the present invention. Thus, in accordance with the present invention, conventional molecular biology, microbiology, recombinant DNA and protein chemistry techniques known to those of ordinary skill of the art can be employed to produce a DNA sequence encoding an ACC and/or FAS polypeptide. Such techniques are explained fully in the relevant literature (see, e.g., Sambrook et al., *Molecular Cloning: A Laboratory Manual*, ($3^{rd}$ ed.) Cold Spring Harbor Laboratory Press, Cold Spring Harbor, N.Y., USA (2001); Glover, *DNA Cloning: A Practical Approach*, ($2^{nd}$ ed.) IRL Press, New York, USA (1995); Gait, *Oligonucleotide Synthesis: A Practical Approach*, IRL Press, New York, USA (1984); Hames & Higgins, *Nucleic Acid Hybridisation: A Practical Approach*, IRL Press, Washington, D.C., USA (1985); Hames & Higgins, *Protein Expression: A Practical Approach*, Oxford University Press, New York, USA, (1999); Masters, *Animal Cell Culture: A Practical Approach*, Oxford University Press, New York, USA (2000); Bickerstaff, *Immobilization of Cells And Enzymes*, Humana Press, Totowa, N.J., USA (1997); Perbal, *A Practical Guide To Molecular Cloning* ($2^{nd}$ ed.) Wiley, New York, N.Y., USA (1988); *Current Protocols in Molecular Biology*, (Ausubel et al., eds.), Greene Publishing Associates and Wiley-Interscience, New York (2002); Ausubel, *Short Protocols in Molecular Biology: A Compendium of Methods from Current Protocols in Molecular Biology*, ($4^{th}$ ed.) John Wiley & Sons, New York, N.Y., USA (1999)). A DNA sequence encoding an ACC and/or FAS polypeptide (including mutants, analogs, and functional equivalents), can be prepared by various molecular biology methods known in the art. Alternatively, a vector comprising an ACC (Ha et al., (1994) *J. Biol. Chem.* 269: 22162-22168) or a FAS sequence (Joshi and Smith, *Biochem J*. (1993) November 15; 296 (Pt 1):143-149) can be employed, some of which are available.

III. Method of Assaying ACC Catalytic Activity

In one aspect of the present invention a method of assaying ACC catalytic activity is provided. In one embodiment, the method comprises: (a) contacting an enzyme mix comprising FAS and a sample known or suspect to comprise ACC with a solid support comprising a scintillant and a linking moiety, the enzyme mix optionally comprising one or more of bicarbonate, Mg, ATP, NADPH and an ACC effector; (b) incubating the enzyme mix with an acetyl CoA mix comprising radiolabeled acetyl CoA, optionally comprising one or more of bicarbonate, Mg, ATP, NADPH and an ACC effector, under suitable reaction conditions, for a desired incubation time; and (c) detecting scintillation signal, wherein scintillation signal is indicative of ACC catalytic activity.

In the first step of the method, an enzyme mix comprising FAS and a sample known or suspect to comprise ACC is contacted with a solid support comprising a scintillant and a linking moiety. The enzyme mix can optionally comprise one or more of bicarbonate, Mg, ATP, NADPH and an ACC effector. The FAS enzyme employed in the present invention may be commercially available or it can be prepared using the methods described herein or those known to those of skill in the art. FIG. 4 describes one process by which FAS can be isolated. The concentration and absolute amount of FAS employed in the assay can depend on the conditions of the assay being performed, but preferably a saturating amount is employed, for example 1 µg/well in a 384-well format, so that the activity is reflective of rate limiting step, which is, the ACC reaction in the coupled enzyme assay.

The enzyme mix comprises a sample known or suspected to contain ACC. When the sample is known to contain ACC, the assay can be performed to measure the amount and/or activity of ACC present in the sample. The assay can also be performed in order to identify the presence and/or activity of ACC in a sample that is not known for certain to contain ACC. Such a sample could be the product of an ACC purification procedure, for example. Thus a sample known to comprise ACC can be assayed to determine the amount and/or activity of ACC in the sample, or the assay can be performed to identify the presence of ACC in a sample in which the presence of ACC is not known.

The enzyme mix of the present invention comprises FAS, which is one of the two enzymes of the coupled enzyme system of the present invention. The enzyme mix can comprise a buffer solution, such as Tris or other buffer, at a pH conducive to ACC and FAS activity, for example pH 7.6. It is desirable to optimize conditions such as temperature so that the enzymes can operate most efficiently. The assay is preferably run at a temperature of about 37° C. An enzyme mix can optionally comprise one or more of bicarbonate, Mg, ATP, NADPH and an ACC effector.

Citrate is one example of a known allosteric activator of ACC and can be optionally included in the enzyme mix. It was found that citrate, while not chemically necessary for the ACC reaction to run, is necessary for other reasons. Therefore, an ACC effector, such as citrate, should be included in the enzyme mix or the acetyl CoA mix, discussed below.

NADPH is a cofactor for the FAS reaction. The FAS reaction requires NADPH to run. Therefore, NADPH should be included in the enzyme mix or the acetyl CoA mix.

During the optimization of the assay of the present invention, it was confirmed that MgATP is required for the carboxylation of biotin in the ACC-catalyzed reaction. Therefore, both magnesium and ATP should be included in either the enzyme mix or the acetyl CoA mix. Magnesium and ATP can be added in any of a range of forms. For example, magnesium can be added in the form of $MgCl_2$. ATP can be added as free ATP or as a complex with magnesium. For instance, in lieu of adding separate magnesium and ATP from separate sources, a solution comprising MgATP can be employed to deliver both components.

Bicarbonate can also be included in the enzyme mix, or as a component of the acetyl CoA mix. The role of bicarbonate in the assay is to provide $CO_2$ for the ACC reaction. Although bicarbonate is a ready source of $CO_2$, any $CO_2$-providing moiety can be employed.

Thus, the enzyme mix comprises at least FAS, but can also comprise ACC, preferably disposed in a buffer, but can also contain all, some or none of bicarbonate, Mg, ATP, NADPH and an ACC effector. The enzyme mix can further comprise other compounds such as ACC and/or FAS cofactors. One example of an enzyme mix is a solution comprising 50 mM Tris-HCl, pH 7.6, 10 mM Na citrate, 4 mM ATP, 10 mM $MgCl_2$, 6 mM $NaHCO_3$, 1 mM EDTA and 100 µM NADPH in addition to FAS and ACC.

ACC effectors, such as citrate, as well as Mg, ATP, acetyl CoA, NADPH or bicarbonate can be added to the enzyme mix or the acetyl CoA mix discussed herein. It is noted that these compounds can be provided in either the enzyme mix or the acetyl CoA mix in any combination. For example, an ACC effector can be added to this enzyme mix, while bicarbonate can be added to the acetyl CoA mix, or vice versa.

The solid support can be any structure that can retain contact with enzyme mix placed in contact with it. One representative embodiment of a solid support is a welled plate. Since the methods of the present invention can be employed in HTS operations, it is preferable to employ a multi-welled plate, such as a 384 well microtiter plate.

The solid support comprises a scintillant. In one embodiment of an assay method of the present invention, the assay is a SPA. Therefore, any scintillant that could be employed in a SPA can be employed in the present invention. Additionally, the scintillant is associated with the support, for example as a coating or partial coating in direct or indirect contact with the solid support. Alternatively, the scintillant can form a component of the plate itself, being essentially integrated within the material of the solid support, for example as a layer.

There are some commercially available solid supports that are provided in a ready-to-use scintillant-coated form. For example, a FLASHPLATE™ is a scintillant-coated commercially available multi-welled plate that can be employed in the present invention. Alternatively, a bead, such as a yttrium silicate bead coated with scintillant (e.g., YSi SPA bead, Amersham Biosciences, Corp, Piscataway, N.J.)) will bind the product palmitic acid and can be employed as a solid support.

A linking moiety forms another element of the present invention. The linking moiety can be any entity that serves to associate a product of the ACC/FAS reaction with the solid support. This association brings the reaction product of the ACC/FAS reaction into proximity with the scintillant, such that the labeled reaction product can initiate scintillation. The linking moiety can be associated with the solid support via a covalent or non-covalent association.

As described herein, one example of a linking moiety is a phospholipid, which can mediate the association of the ACC/FAS reaction product, palmitic acid, with the solid support. This association is mediated by a hydrophobic interaction. Although a phospholipid has been presented in the Examples and Drawings as a linking moiety, any compound can be employed, as long as that compound serves to bring the reaction product of the ACC/FAS reaction, palmitic acid, close enough to the scintillant associated with the solid support to induce scintillation.

The contacting step can be accomplished by any means, for example by pipetting a volume of the enzyme mix onto the solid support (e.g., a well of a welled plate). Automated systems can be employed in HTS operations to facilitate the contacting step.

In the next step of the method, the enzyme mix is incubated with an acetyl CoA mix comprising labeled acetyl CoA, optionally comprising one or more of bicarbonate, Mg, ATP, NADPH, and an ACC effector under suitable reaction conditions, for a desired incubation time. The acetyl CoA mix can be incubated with the enzyme mix on the solid substrate. The acetyl CoA mix can comprise, in addition to labeled acetyl CoA, other components, such as unlabeled acetyl CoA. It can be desirable to include unlabeled acetyl CoA because the substrate has to be used at or above the $K_m$ value in an enzyme reaction, and if radiolabeled material is used exclusively, this comparatively large amount of radioactive material in the reaction mixture can be economically and environmentally undesirable, and is unnecessary to generate a detectable scintillation signal. The acetyl CoA mix can further comprise a buffered solution, and in many situations it will be preferable to maintain the acetyl CoA mix in the same buffer as the enzyme mix. Tritiated acetyl CoA is commercially available, for example from Amersham, Piscataway, N.J.

It is again noted that MgATP, bicarbonate and NAPDH are necessary for the ACC/FAS coupled enzyme reaction to proceed. Therefore these components should be included in either the enzyme mix or the acetyl CoA mix. An ACC effector, such as citrate, can also be included in the acetyl CoA mix. An ACC effector can be added to either the enzyme mix or the acetyl CoA mix.

"Suitable reaction conditions" are conditions that maintain FAS and ACC in a functional form. These conditions can be such that the activity of one or both of the enzymes is not maximal, but it is generally preferable that conditions allowing for maximum enzyme activity are maintained whenever possible. More particularly, it is preferable to provide adequate amounts of substrates, cofactors and effectors, and to provide conditions such that the activity of any ACC present in the reaction mixture will not be limited by the availability of these compounds. In other words, it is preferable to make enzyme concentration the rate limiting factor, rather than substrate concentrations. Beyond buffering conditions, suitable reaction conditions comprise maintaining the presence of any effectors and optimal temperature, which in the present invention is about 37° C. In the present invention incubation periods can vary from none to two or more hours. The inventors have found that an incubation period of about two hours is sufficient for the assay to provide optimal results.

Lastly, after the incubation period, scintillation signal is detected. As described herein, in an assay of the present invention scintillation signal is generated as a result of positioning the radiolabled product of the ACC/FAS reaction, namely [$^3$H] palmitic acid, close enough to the scintillant, which is associated with the solid support, to induce scintillation, which is then detected.

Generally, a scintillation counter of some form will be employed in the detection step. The method of detection can vary and can be dependent on the nature of the solid support. For example, when the solid support is a FLASHPLATE™ or other welled plate, the scintillation signal can be detected using an automated plate reader, such as a TOPCOUNT™ plate reader. The presence of scintillation signal is indicative of ACC catalytic activity. When the assay is performed detectable scintillation signal will be generated if there is any ACC present; if there is no ACC present in the sample, no scintillation signal will be present. The amount of scintillation signal can be expressed in counts per minute (cpm). Another form of solid support that can be employed in the present invention is an IMAGE FLASHPLATE™ which is a 384-weled shallow microplate coated with a scintillant that emits in the red region and the scintillation signal is detected in imaging plate readers, such as LEADSEEKER™ or VIEWLUX™ plate reader. The amount of scintillation signal can be expressed in intrinsic optical density (IOD).

IV. Method of Identifying a Modulator of ACC Catalytic Activity

In another aspect of the present invention a method of identifying a modulator of ACC catalytic activity is disclosed. This embodiment of the present invention can be employed in a HTS setting. In one embodiment of the assay, the method comprises initially measuring ACC catalytic activity in the absence of a test compound. This measurement can be made by employing a method of measuring ACC activity of the present invention. The measurement can also be made by employing a known ACC assay, such as a $^{14}CO_2$-fixation assay, although for purposes of consistency, it is preferable that the measurement be made using an assay of the present invention. This measurement serves as a baseline against which the effect of a test compound is gauged.

Next, an enzyme mix comprising ACC, FAS and a test compound is contacted with a solid support comprising a scintillant and a linking moiety, the enzyme mix optionally comprising one or more of bicarbonate, Mg, ATP, NADPH and an ACC effector. As noted herein, ACC and FAS can be isolated as described herein and as shown in FIG. 4. The roles of bicarbonate, Mg, ATP, NADPH and ACC effectors are described herein, as well as their availability and suitable concentrations for use. Representative concentrations and amounts of the enzymes and compounds for use in the methods of the present invention are also provided, for example in Example 2. These compounds can be added either as components of the enzyme mix or the acetyl CoA mix.

A test compound can comprise a compound known or suspected to modulate ACC activity. The test compound can be solubilized in a solvent, such as DMSO. As FIG. 11 indicates, the presence of up to 0.3% DMSO does not affect ACC activity, while DMSO concentrations of about 1% and above can have the effect of inhibiting ACC activity. Thus, a test compound can be solubilized in DMSO, which is subsequently serially diluted to a desired concentration, for example in about 0.3% DMSO. If a solvent other than DMSO is employed optimization procedures can be employed to determine levels of that solvent that the assay can tolerate. Guidance is provided in this regard in the Examples, and a protocol similar to that employed in the case of DMSO can be used to optimize the assay for a test compound disposed in a solvent other than DMSO.

Examples of suitable solid supports are provided herein. The only requirement for a solid support is that the support comprises a scintillant and a linking moiety. As is the case with all assays of the present invention, the scintillant can be associated with the support either on the surface of the support, e.g., it can be applied to the surface of the support, or it can be integrally associated with the support. A multi-welled plate, such as FLASHPLATE™, is the preferred solid support. As described herein, in any of the methods or kits of the present invention a bead, such as a yttrium silicate bead coated with scintillant (e.g., YSi SPA bead, Amersham Biosciences, Corp, Piscataway, N.J.) will bind the product palmitic acid and can be employed as a solid support.

The linking moiety can be any entity adapted to facilitate an association between the labeled palmitic acid produced by the coupled enzyme reaction, and the scintillant associated with the solid support. The linking moiety should bring the labeled palmitic acid into proximity with the scintillant, such that any labeled palmitic acid present induces scintillation. In one embodiment of the assay, a phospholipid is employed as a linking moiety, although a linking moiety need not be limited to a phospholipid.

The enzyme mix and the test compound are then incubated with an acetyl CoA mix comprising radiolabeled acetyl CoA, optionally comprising one or more of bicarbonate, Mg, ATP, NADPH and an ACC effector, under suitable reaction conditions, for a desired incubation time. The label associated with the acetyl CoA can be any label adapted to induce scintillation, for example [$^3$H] acetyl CoA, as described herein. The various components of the acetyl CoA mix can be added at the concentrations provided herein. As in the case of the enzyme mix, these compounds need only be present in the final reaction mixture (i.e., after the acetyl CoA mix and the enzyme mix have been contacted with the solid support), and can be added as components of either the enzyme mix or the acetyl CoA mix.

Suitable reaction conditions are provided, for example, in the Examples. Suitable conditions are those conditions that are favorable for ACC and FAS activity. Considerations can include pH (a pH of about 7.6 is preferred) and temperature (a temperature of about 37° C. is preferred). The incubation period is variable, but can be selected to provide adequate time for the ACC/FAS reaction to proceed to completion. It has been found that an incubation period of about two hours is sufficient for the assay when it is performed as described herein, although under different conditions, such as different reaction conditions and different substrate and cofactor concentrations, longer or shorter periods may be optimal.

Following the incubation period, scintillation signal from the sample comprising the test compound is detected. The detection can employ a plate reader to detect scintillation signal, such as a TOPCOUNT™ reader, when the solid support comprises a welled plate. When a multi-welled plate is employed as a solid support, scintillation signal can be detected at any desired rate, for example a rate of about 2 minutes per well. When employing different conditions, including different enzyme concentrations, an advantage of the methods of the present invention is that a plate reader can be employed, which enables high-throughput screening.

In a further step of the method, scintillation signal generated in the presence of the test compound is correlated with ACC catalytic activity, wherein a difference between the ACC catalytic activity detected in the presence of the test compound compared to ACC catalytic activity detected in the absence of the test compound indicates the test compound is a modulator of ACC catalytic activity. This correlation can be quantitative, and the activity of ACC in the presence and absence of the test compound can be compared in terms of counts per minute (CPM).

V. Kit for Assaying ACC Catalytic Activity

In another aspect of the present invention, a kit for assaying ACC catalytic activity is disclosed. In one embodiment, the kit comprises a container containing an enzyme mix comprising FAS, and optionally containing one or more of bicarbonate, Mg, ATP, NADPH, and an ACC effector. The kit also comprises a container containing an acetyl CoA mix comprising radiolabeled acetyl CoA, and optionally comprising one or more of bicarbonate, Mg, ATP, NADPH, and an ACC effector. Together the contents of the containers should contain each of the chemically necessary components for the ACC/FAS coupled enzyme reaction, including at least the FAS itself. ACC can be included in the kit in a separate container, or in the same container as the FAS, and employed in an assay to determine the effect of a test compound on ACC activity. Alternatively, ACC can be omitted from the kit and assay when it is desired to determine the presence of ACC in a sample. Thus, the kit can be employed in either of these types of assays.

The kit also comprises a solid support comprising a scintillant and a linking moiety. Representative solid supports, scintillants and linking moieties are described herein. Solid supports in which the scintillant and linker are both pre-associated with the solid support can be purchased commercially. In one embodiment of the kit, the linking moiety can be provided separately from the solid support and can be associated with the solid support by a user prior to running an assay.

The kit can also comprise instructions to guide a user through the steps of performing and interpreting an assay. The components of the kit can be provided in concentrated solutions or in ready-to-use aliquots.

VI. Conclusions

An assay of the present invention offers many advantages over known methods of assaying ACC activity. First, the assay of the present invention is not as cumbersome as many of the prior art methods. The $^{14}CO_2$ fixation assay, for example, requires specialized equipment for working with gases, which can be expensive and technically challenging to operate. Further, the assay of the present invention can be performed on a single solid support and does not require any transfer of materials from the support itself.

Further, the assay of the present invention is a single step assay. In an assay of the present invention, once the enzymes, substrates and samples are contacted with the solid support, scintillation signal induced by the presence of the labeled product can be detected without removing the product from the wells of the plate. The $^{14}CO_2$ fixation assay, for example, is a multistep process, which can be tedious and is not feasible for HTS operations.

Additionally, an assay of the present invention is rapid, making it suitable for use in a HTS setting. Most known methods of assaying for ACC are time-consuming and cannot be employed or adapted to perform adequately in a HTS operation.

Continuing, an assay of the present invention also requires only low levels of radiation, making the assay preferable to those prior art methods employing higher levels of radiation.

Still further, the assay is relatively inexpensive to run. The enzyme(s) required for the assay can be isolated as described herein, or they can be purchased. Moreover, only small amounts of enzyme are required for the present assay. Other reagents that can be employed in the assay can be purchased inexpensively.

EXAMPLES

The following Examples have been included to illustrate preferred modes of the invention. Certain aspects of the following Examples are described in terms of techniques and procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

Enzyme Preparation

ACC and FAS were purified by a rapid purification procedure (FIG. 4) from frozen livers of rats that were fasted for 36 hours and fed with fat-free carbohydrate diet for 48 hours (Seethala & Benjamin, (1983) *Preparative Biochem.* 13:475-488; Jamil & Madsen, (1987) *J. Biol. Chem.* 262: 630-637). The livers were thawed and washed with PBS buffer and minced into small pieces in 3 volumes of buffer A (50 mM potassium phosphate buffer, pH 7.5, 1 mM EDTA, 0.1 mM EGTA, 10 mM β mercaptoethanol, 5 mM benzamidine, protease inhibitor cocktail (10 μM TLCK, 1 μg/ml of leupeptin, aprotinin, pepstatin, AEBSF, pepstatin A and trypsin inhibitor) and 250 mM sucrose) and homogenized in Polytron 4×1 min. All the operations were done at 4° C. or on ice. The homogenate was centrifuged at 5000×g for 5 min. The supernatant 1 was saved and the pellet suspended in one volume of buffer A and rehomogenized in Polytron 4×1 min and centrifuged at 5000×g for 5 min. The pellet was discarded and the supernatant 2 was combined with the supernatant 1 and centrifuged at 25,000×g for 30 min. The pellet was discarded and the supernatant 3 was centrifuged at 100,000×g for 60 min. To the high-speed supernatant ammonium sulfate was added to 44% saturation (25 g/100 ml) adjusting pH with ammonia/1M KOH and centrifuged at 25,000×g for 20 min. The pellet was dissolved ($\frac{1}{5}^{th}$ original volume) in buffer B (100 mM Tris-HCl buffer, pH 7.5, 0.5 M NaCl, 1 mM EDTA, 0.5 mM dithiothreitol, protease inhibitor cocktail, and 5% glycerol) and centrifuged at 25,000×g for 20 min. To the supernatant in a roller bottle, monomeric avidin Sepaharose freshly regenerated and equilibrated in buffer B was added and mixed on a bottle roller over night. The mixture was filtered on a sintered funnel collecting the flow-through for the purification of FAS. Avidin Sepaharose was washed with 30 volumes of buffer B and loaded into a column. ACC was eluted with 5 mM biotin in buffer B collecting 3 ml fractions. The fractions containing ACC activity were pooled, ammonium sulfate was added to 44% saturation and centrifuged at 25,000×g for 20 min. The pellet was dissolved in buffer C (100 mM Tris-HCl buffer, pH 7.5, 1 mM EDTA, 0.5 mM dithiothreitol, protease inhibitor cocktail, and 20% glycerol) and dialyzed against 100 volumes of buffer C with an additional change of buffer. The dialyzed ACC enzyme was aliquoted into small volumes and stored at –80° C.

FAS was purified from the flow-through fraction of avidin-Sepharose. Polyethylene glycol (PEG; 50% stock in $H_2O$) was added to the avidin-Sepharose flow-through to a final concentration of 10% and centrifuged at 25,000×g for 20 min. To the supernatant, 50% PEG was added to a final concentration of 15% and centrifuged at 25,000×g for 20 min. The pellet was washed gently with cold water and dissolved ($\frac{1}{10}^{th}$ original volume) in buffer D (50 mM potassium phosphate buffer, pH 7.5, 1 mM dithiothreitol, protease inhibitor cocktail and 5% glycerol). The 10-15% PEG fraction was centrifuged and the supernatant was mixed with DEAE-Sephacel equilibrated in buffer D and mixed on a bottle roller for 2 hours. The mixture was filtered on a sintered funnel and washed with 25 volumes of buffer D and FAS is eluted with 6 volumes of 200 mM potassium phosphate in buffer D. To the eluate 50% PEG was added to a final concentration of 15%, centrifuged at 25,000×g for 20 min. The pellet was dissolved ($\frac{1}{20}^{th}$ original volume) in buffer C, aliquoted into small volumes and stored frozen at –80° C.

Example 2

Solution Preparation and Assay Conditions

Assay Buffer: 50 mM Tris-HCl, pH 7.6, 10 mM Na Citrate, 4 mM ATP, 10 mM $MgCl_2$, 6 mM $NaHCO_3$, 1 mM EDTA, 100 μM NADPH.

5×[$^3$H]-Acetyl CoA mix: To [$^3$H]-Acetyl CoA, unlabeled acetyl CoA was added to a total concentration of 100 μM in the assay buffer. The [$^3$H]-acetyl CoA mix in the final reaction was 20 μM with 0.25 μCi per assay (specific activity of 250 μCi/μmol).

Enzyme mix: To each well, 0.1 μg of rat acetyl CoA carboxylase 1 (rACC) and 2 μg of rat fatty acid synthase (rFAS) in a total volume of 35 μl in the assay buffer was added.

Compound Dilution: Compounds were dissolved in 100% DMSO to obtain 10 mM stock solution. A serial dilution of the compounds in 100% DMSO was made first. Then the compounds were diluted 1:33.3 in buffer to obtain 10× compound solution in 3% DMSO. From this intermediate dilution, a further 10× dilution was made in the assay, resulting 0.3% final DMSO concentration in the assay.

The sequence of addition of the solution mixtures into each well of a custom 384-well phospholipid coated FLASHPLATE™ was as follows:

Step 1: Add 35 μl of enzyme mix in assay buffer.
Step 2: Add 5 μl of 3% DMSO or 10× compound in 3% DMSO.
Step 3: Incubate at room temperature for 10 min.
Step 4: Add 10 μl of 5× [$^3$H]-acetyl CoA mix to start the reaction.
Step 5: Incubate the plate at 37° C. for 2 hours.
Step 6: Count the plate in a TOPCOUNT™ NXT for 2 min/well.

Example 3

Reaction Time Course

In a representative optimization of the ACC/FAS-coupled SPA assay, $MgCl_2$, ATP, $NaHCO_3$, sodium citrate, acetyl CoA, and NADPH were added to assay buffer and the reaction was initiated with the addition of ACC and FAS. For determining the compound inhibition, $MgCl_2$, ATP, $NaHCO_3$, sodium citrate, ACC, FAS, and NADPH were added to the assay buffer and the reaction was started by the addition of [$^3$H]-acetyl CoA mix.

Figure 5:
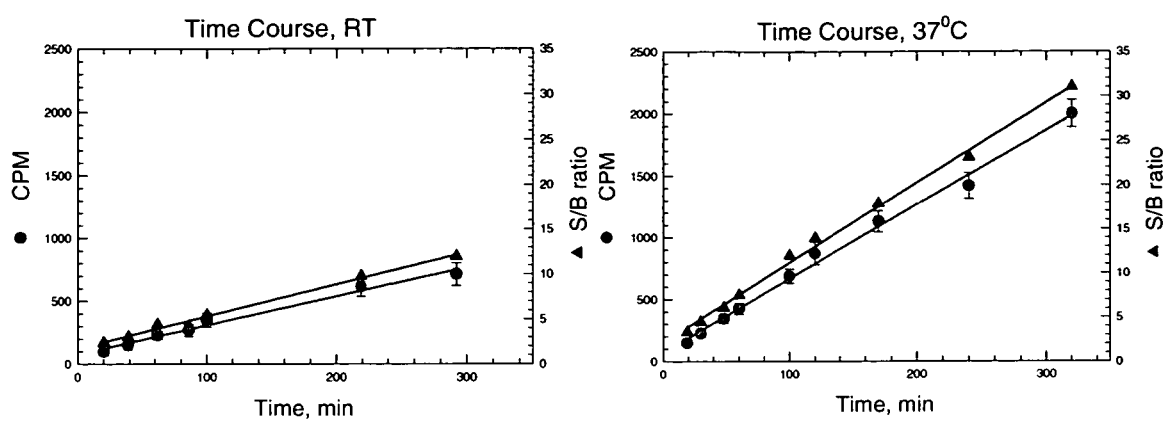
FIG. 5 comprises two plots depicting a time course of ACC activity at room temperature (left panel) and at 37° C. (right panel).

The time course of reaction was studied at room temperature (RT, 21° C.) and at 37° C. The reaction was linear up to 5 hours at both temperatures (FIG. 5). However, the maximum signal to background (S/B) was higher at 37° C. than at RT (S/B=12 at RT and S/B=32 at 37° C.). The preferred incubation condition was 37° C. for 2 hours. There was minimal signal change when the plates were kept at 4° C. after incubation at 37° C. (Table 1). Thus, the reaction can be quenched by chilling the plate at 4° C. When a large number of plates are processed after incubation at 37° C. the plates can be chilled at 4° C. until ready to read.

TABLE 1

Quenching the reaction by cooling at 4° C.

|  | RT | RT | 37° C. | 37° C. |
|---|---|---|---|---|
| Time, min | 292 | O/N (4° C.) | 300 | O/N (4° C.) |
| Avg CPM | 779 | 883 | 2068 | 2131 |
| Avg Bl | 65 | 83 | 67 | 69 |
| Avg net CPM | 714 | 800 | 2001 | 2062 |
| AVEDEV | 90 | 84 | 111 | 105 |
| S/B | 12.0 | 10.6 | 31 | 30.7 |

Example 4

Enzyme Titration

Figure 6:
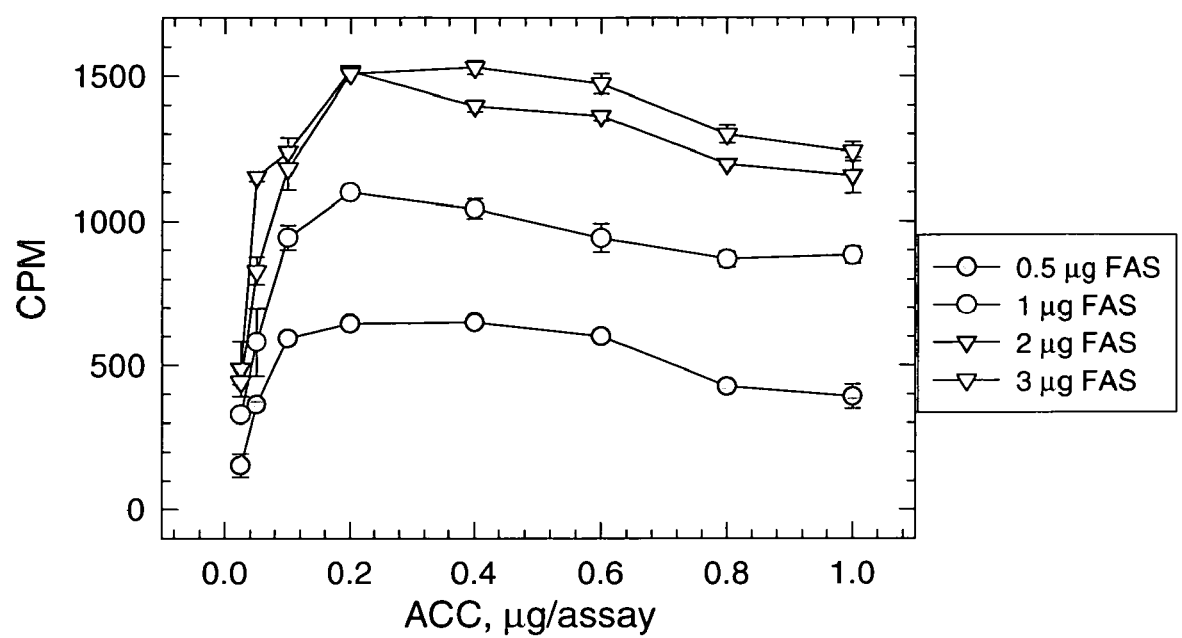
FIG. 6 is a plot depicting the results of titrating ACC at different concentrations of FAS.

To determine the optimal concentrations of ACC and FAS for the best signal, the reaction was titrated with ACC (purified through the avidin-Sepharose step) at different FAS (purified through DEAE-Sephacel step) concentrations (FIG. 6). The signal increased with increasing FAS from 0.5 μg reaching a maximum at 2.0 μg. At 3 μg FAS the signal remained the same as at 2 μg and at higher concentrations the activity decreased. At each FAS concentration, the activity increased with increasing ACC and reached saturation at about 0.2 μg. For all the 384-well FLASHPLATE™ assays in this study 0.1 μg ACC and 2.0 μg FAS were used.

Example 5

Reagent Titrations

To detect ACC activity ATP, bicarbonate, $Mg^{2+}$, citrate and acetyl CoA are required. In the absence of any one of these no activity is detected in this assay. The $K_m$ for the substrates, acetyl CoA, ATP and bicarbonate and the $K_{act}$ for the other effectors, $MgCl_2$, and citrate were determined by assaying activity at various concentrations of one reagent and saturating concentrations of all the others (10 mM sodium citrate, 4 mM ATP, 10 mM $MgCl_2$, 6 mM $NaHCO_3$) except acetyl CoA (at 20 μM, approximately 0.5× $K_m$ level) at 37° C.

Figure 7:
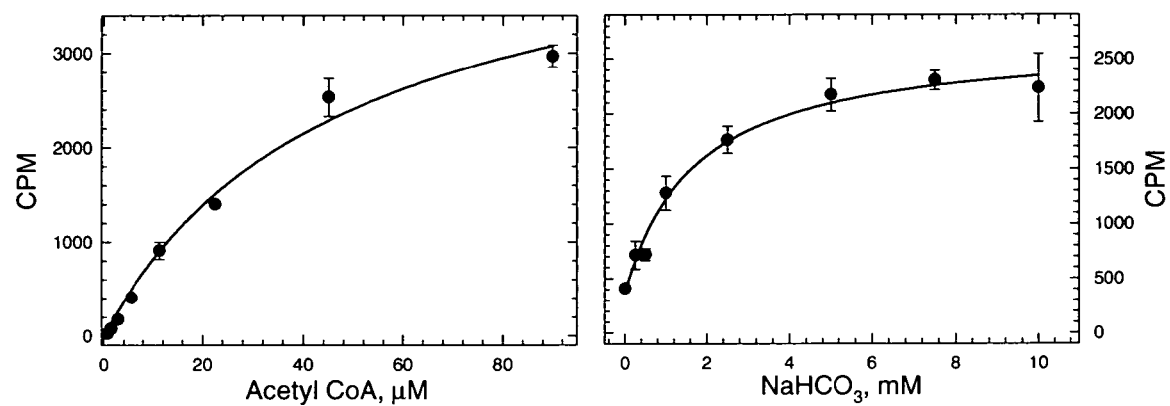
FIG. 7 comprises two plots depicting the dependence of enzyme activity on [$^3$H]acetyl CoA (left panel) and bicarbonate (right panel) concentrations.
Figure 8:
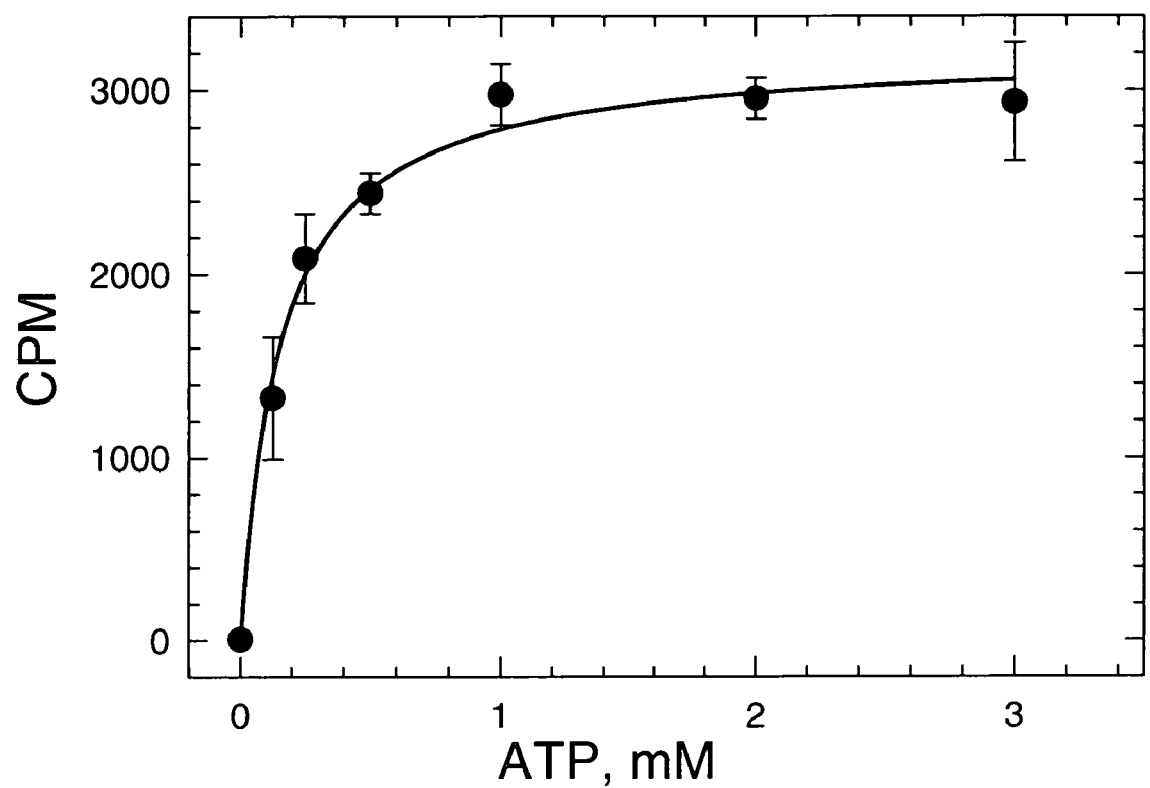
FIG. 8 is a plot depicting the dependence of ACC activity on ATP concentration.

The enzyme activity increased with increasing concentrations of $NaHCO_3$ and reached saturation at 8 mM. Because of dissolved $CO_2$ in the water and buffers, there was residual activity even in the absence of added $NaHCO_3$. The $K_m$ for $NaHCO_3$ from the saturation curve was 1.7 mM (FIG. 7B). The enzyme activity increased with increasing concentration of acetyl CoA and reached saturation at 100 μM (FIG. 7A). No enzyme activity was detectable without added acetyl CoA. The $K_m$ for acetyl CoA from the curve was 47 μM. [$^3$H] acetyl CoA was used at 20 μM (at about 0.5× $K_m$) to direct the screening for inhibitors of acetyl CoA carboxylation step (transcarboxylation half reaction step). Mg-ATP is required in the carboxylation of biotin enzyme step. FIG. 8 suggests that there is a requirement for Mg-ATP for the first step of the ACC catalyzed reaction. The enzyme activity showed a standard titration for ATP dependency, reaching saturation at 1 mM. The $K_m$ for ATP was 0.15 mM.

Example 7

Figure 9:
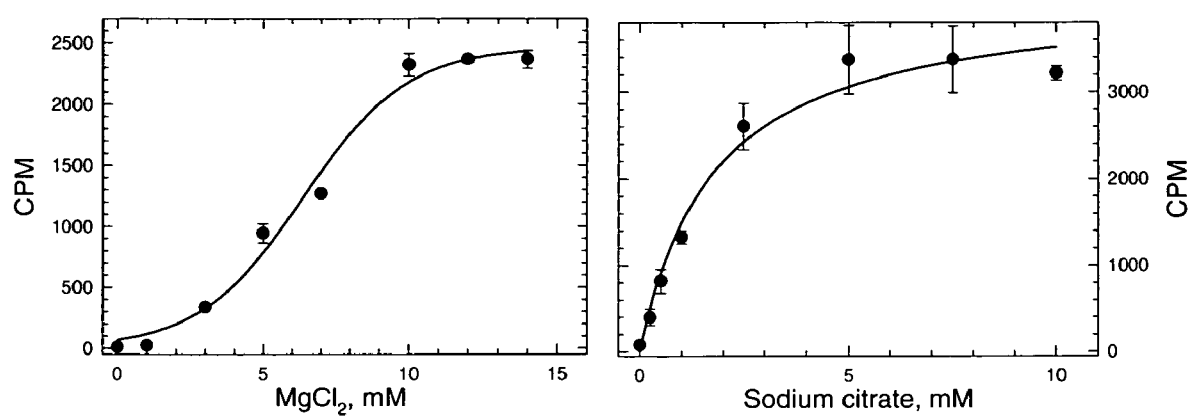
FIG. 9 comprises two plots depicting the dependence of enzyme activity on $MgCl_2$ (left panel) and citrate (right panel) concentrations.

$K_{act}$ for Effectors $Mg^{2+}$ chelates with ATP to form an active Mg-ATP complex, which is required for the first biotin carboxylation half reaction step. No detectable activity was found at 1 mM $MgCl_2$ and activity increased with concentration reaching saturation at 10 mM. The $K_{act}$ for $MgCl_2$ (half-maximal saturation value) from the curve is 6.3 mM, Citrate is an allosteric activator of ACC. FIG. 9 indicates that citrate is required for catalysis. The $K_{act}$ for citrate was determined to be 1.67 mM under the assay conditions. In this study, citrate was maintained at a saturating concentration of 10 mM, above which the catalytic rate was not further increased. In general, $Mg^{2+}$ dependent enzymes such as ACC require a slight excess of free $Mg^{2+}$ for maximal activity. Since both citrate and ATP are good chelators of $Mg^{2+}$ it is generally desirable to have the total $Mg^{2+}$ concentration at 1 mM in excess of the total citrate plus ATP level (15 mM under these assay conditions). It is clear from the titrations shown in FIG. 9, however, that 10 mM total $Mg^{2+}$ is sufficient for maximal activity.

Example 8

$K_m$ for FAS Cofactor NADPH

The malonyl CoA formed in the ACC reaction and acetyl CoA are co-substrates for FAS. The malonyl CoA synthesized by ACC is employed by FAS in the ACC/FAS coupled assay, and the $K_m$ values for the FAS substrates, acetyl CoA and malonyl CoA, can not easily be determined in the presence of ACC. In the ACC/FAS coupled assay, acetyl CoA is a substrate for ACC and it can be challenging to estimate the acetyl CoA remaining. The malonyl CoA formed in the ACC reaction is utilized immediately and does not accumulate.

Figure 10:
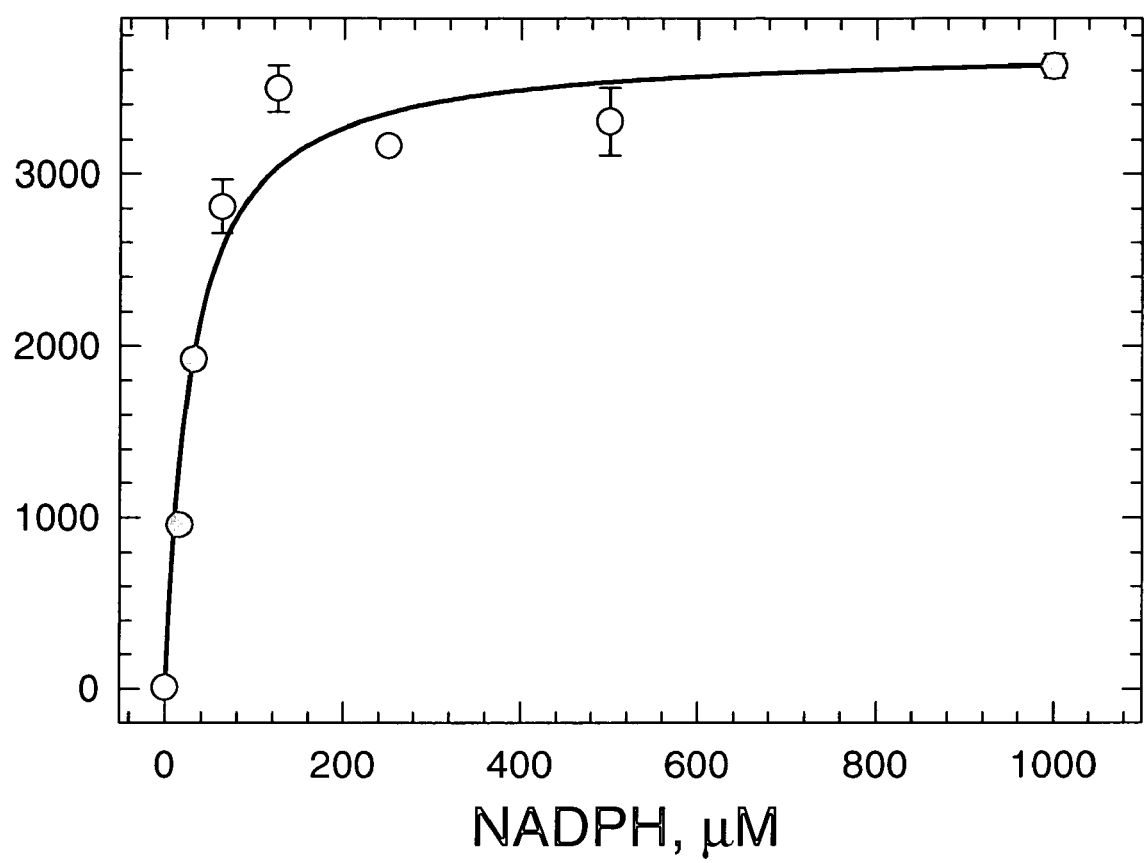
FIG. 10 is a plot depicting the dependence of the assay of the present invention on NADPH concentration.

The $K_m$ values for these FAS substrates can be determined independently. In the present study, the dependence of FAS activity on NADPH was determined by varying the cofactor concentration (FIG. 10). The results show a requirement for NADPH for the final signal, confirming that the signal is due to ACC activity followed by FAS activity. The $K_m$ determined for NADPH from the curve is 28 μM. In this study, NADPH was maintained at saturating concentration of 100 μM.

The $K_m$ values determined by the ACC/FAS coupled SPA were comparable to the literature values determined by $^{14}CO_2$-fixation assay, indicating that the ACC/FAS coupled enzyme assay is truly measuring the ACC activity. In the absence of the ACC substrates or any of the effectors there is no detectable signal.

Example 9

Effect of DMSO

Figure 11:
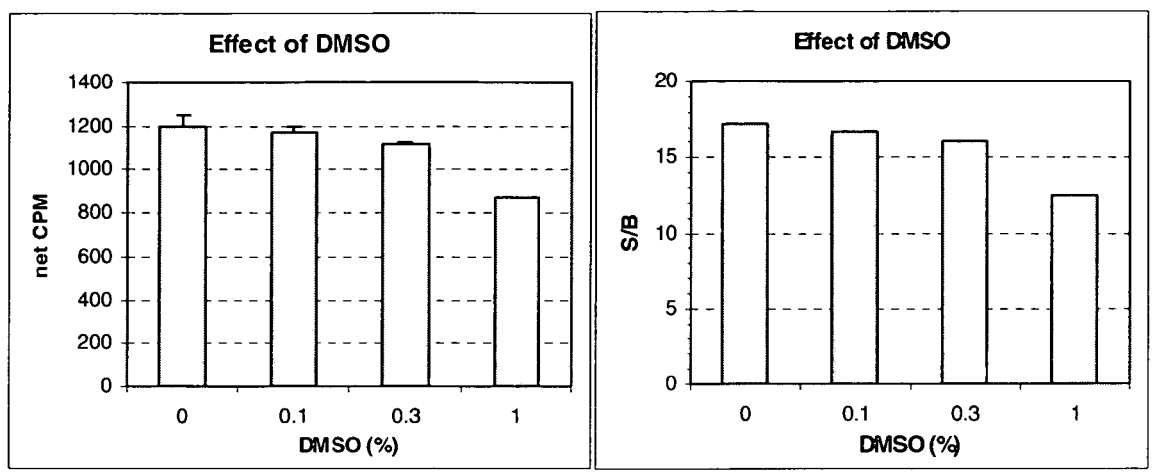
FIG. 11 comprises two bar graphs depicting the effect of DMSO on an assay of the present invention in terms of cpm (left panel) and S/B (right panel).

For screening in drug discovery, compounds are routinely dissolved in 100% DMSO and then further diluted to 1% or lower DMSO in the final assay. The effect of DMSO on the ACC/FAS coupled assay was studied. As shown in FIG. 11, DMSO concentrations up to 0.3% have no significant effect on the activity of FAS or ACC. At 1% DMSO, the total signal decreased 25% and the S/B was reduced from 15 to 12 with a greater inhibition observed at higher concentrations. Therefore, it may be desirable to keep the final DMSO concentrations in the assay below 0.3%, and not to exceed 1%.

Example 10

Effect of Reagents

Figure 12:
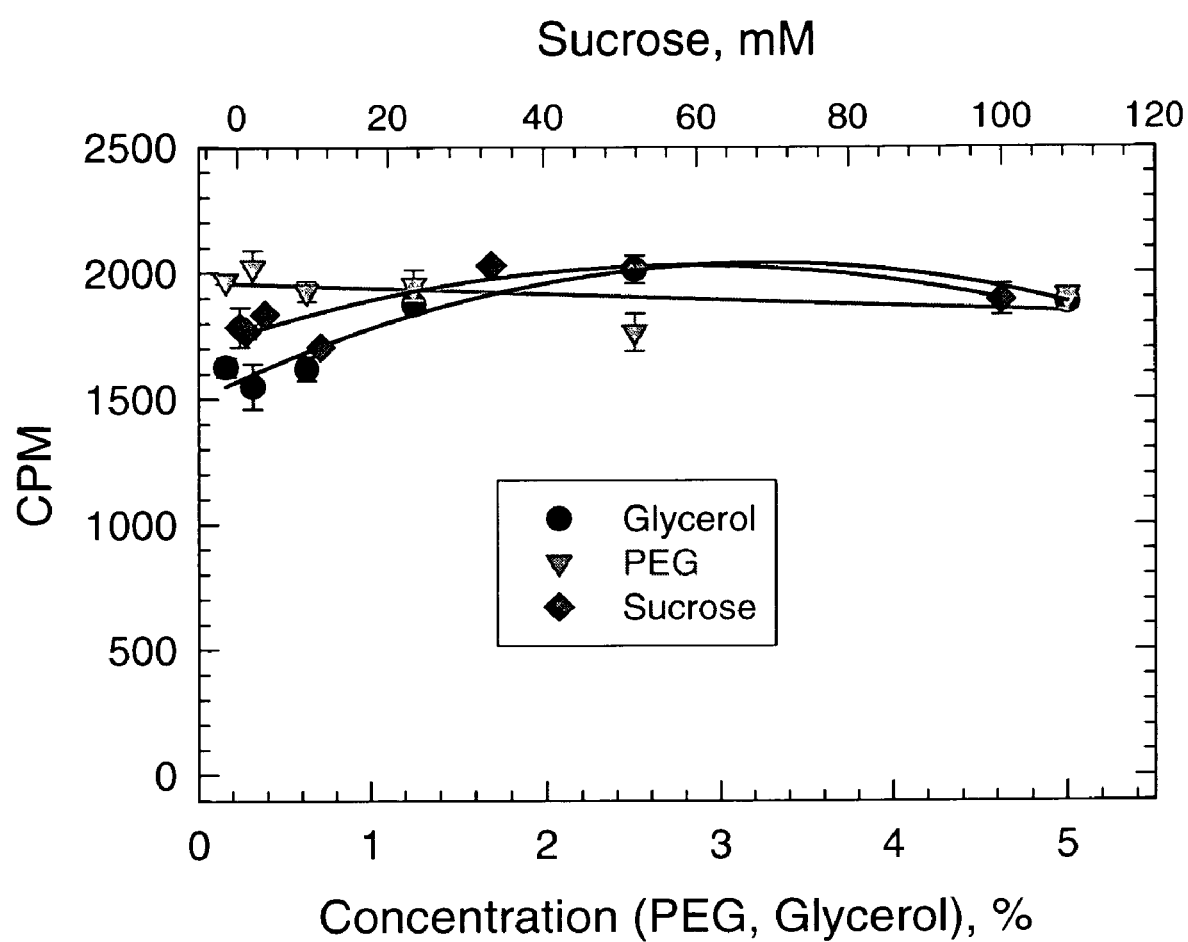
FIG. 12 is a plot depicting the effect of glycerol, PEG and sucrose on an assay of the present invention.

Buffers containing sucrose, glycerol and polyethylene glycol (PEG) were used in the purification of ACC and FAS. In addition, the purified enzymes were stored in buffers containing 20% glycerol to increase long-term stability. In view of this, the effects of glycerol, sucrose and PEG on the enzyme activities were studied with the ACC/FAS coupled SPA. As shown in FIG. 12, none of these reagents have any significant effect on the enzyme reaction.

REFERENCES

The references cited herein are incorporated herein by reference to the extent that they supplement, explain, provide a background for or teach methodology, techniques and/or compositions employed herein. All cited patents, including patent applications, and publications referred to in this application are herein expressly incorporated by reference. Also expressly incorporated herein by reference are the contents of all citations of GENBANK® accession numbers, LocusID, and other computer database listings, as well as the contents of any Sequence Listing associated herewith.

It will be understood that various details of the invention may be changed without departing from the scope of the invention. Furthermore, the foregoing description is for the purpose of illustration only.

What is claimed is:

1. A method for identifying modulators of human acetyl coenzyme A carboxylase (ACC) comprising:
    a) adding a control mixture to a control reaction vessel comprising a solid support, a scintillant and a linking moiety; wherein said control mixture excludes exogenous malonyl Co A and comprises purified human ACC, purified recombinant fatty acid synthase (FAS), magnesium, adenosine tri-phosphate (ATP), NaHCO$_3$, citrate, dimethyl sulfoxide (DMSO), and reduced adenine nicotinamide dinucleotide phosphate (NADPH);
    b) adding a test mixture to a test reaction vessel comprising a solid support, a scintillant and a linking moiety; wherein said test mixture excludes exogenous malonyl Co A and comprises purified human ACC, purified recombinant fatty acid synthase (FAS), magnesium, adenosine tri-phosphate (ATP), NaHCO$_3$, citrate, a test agent having unknown biological activity, DMSO, and reduced adenine nicotinamide dinucleotide phosphate (NADPH);
    c) adding tritiated acetyl coenzyme A ($^3$H-acetyl CoA) to said control reaction vessel and said test reaction vessel and incubating said vessels for an incubation period;
    d) obtaining a tritiated product in said control and test reaction vessels;
    e) measuring the radioactivity associated with said tritiated product in the control reaction vessel and test reaction vessel; and
    f) comparing the radioactivity levels in the control reaction vessel and test reaction vessel whereby a difference in radioactivity in the test reaction vessel indicates that said test agent is a modulator of ACC activity.

2. The method of claim 1 wherein the ACC is ACC1 or ACC2.

3. The method of claim 1 wherein said control or test reaction vessels are selected from the group consisting of multi-welled plates and beads.

4. The method of claim 1 wherein the linking moiety is a phospholipid.

5. The method of claim 1 wherein the test agent is diluted in DMSO before being contacted with the solid support.

6. The method of claim 1 wherein the method is employed in a high throughput screening operation.

7. The method of claim 1 wherein the incubation period is about two hours at about 37 degrees Celsius.

8. The method of claim 1 wherein about 0.1 μg of purified ACC and 2.0 μg of FAS are used.

9. The method of claim 1 wherein the magnesium concentration is about 10 mM.

10. The method of claim 1 wherein the NADPH concentration is maintained at about 100 μM.

* * * * *